US008172847B2

(12) United States Patent
Dziedzic et al.

(10) Patent No.: US 8,172,847 B2
(45) Date of Patent: May 8, 2012

(54) IN-LINE ROD REDUCTION DEVICE AND METHODS

(75) Inventors: Sara Dziedzic, Dorchester, MA (US); Garth G. Baker, Somerset, MA (US); Shawn D. Stad, Fall River, MA (US); Nicholas Pavento, Dorchester, MA (US); Paul Beaudoin, Derry, NH (US)

(73) Assignee: DePuy Spine, Inc., Raynham, MA (US)

( * ) Notice: Subject to any disclaimer, the term of this patent is extended or adjusted under 35 U.S.C. 154(b) by 1174 days.

(21) Appl. No.: 11/693,077

(22) Filed: Mar. 29, 2007

(65) Prior Publication Data

US 2008/0243190 A1   Oct. 2, 2008

(51) Int. Cl.
*A61B 17/88* (2006.01)

(52) U.S. Cl. ........................................ 606/86 A; 606/99

(58) Field of Classification Search ............... 606/86 A, 606/99, 264–278, 300, 305–308
See application file for complete search history.

(56) References Cited

U.S. PATENT DOCUMENTS

| 410,780 A | 9/1889 | Cahn |
| 1,470,313 A | 10/1923 | Woolen |
| 1,628,144 A | 5/1927 | Herrmann |
| 1,709,766 A | 4/1929 | Bolton |
| 1,889,330 A | 11/1932 | Humes et al. |
| 1,925,385 A | 9/1933 | Humes et al. |
| 2,113,246 A | 5/1937 | Wappler |
| 2,248,054 A | 7/1941 | Becker |
| 2,248,057 A | 7/1941 | Bond |
| 2,291,413 A | 7/1942 | Siebrandt |
| 2,370,407 A | 2/1945 | McCartney |
| 2,800,820 A | 7/1957 | Retterath |
| 3,960,147 A | 6/1976 | Murray |
| 4,237,875 A | 12/1980 | Termanini |
| 4,271,836 A | 6/1981 | Bacal et al. |

(Continued)

FOREIGN PATENT DOCUMENTS

DE    4238339    5/1994

(Continued)

OTHER PUBLICATIONS

International Search Report (PCT/US2008/068515) dated Jan. 2, 2009.

(Continued)

*Primary Examiner* — Eduardo C Robert
*Assistant Examiner* — Ellen C Hammond
(74) *Attorney, Agent, or Firm* — Nutter McClennen & Fish LLP

(57) ABSTRACT

The present invention provides methods and devices for placing a spinal fixation rod into a rod receiving opening in a spinal anchor and installing a fastener to secure the rod to the spinal anchor. In one embodiment, the system can include a cap having a bore extending therethrough, an elongate drive rod that is adapted to extend through the bore, and a fastener that is disposed on a distal portion of the drive rod. The cap can include a driving element that is adapted to cooperate with a complementary driving element disposed on the rod to form a driving mechanism. Actuation of the driver mechanism can be effective to advance the drive rod through the cap to thereby reduce a spinal rod into a rod receiving opening of the spinal anchor and install the fastener to secure the rod to the spinal anchor.

15 Claims, 12 Drawing Sheets

U.S. PATENT DOCUMENTS

| | | | |
|---|---|---|---|
| 4,411,259 A | 10/1983 | Drummond | |
| 4,445,513 A | 5/1984 | Ulrich et al. | |
| 4,655,223 A | 4/1987 | Kim | |
| 4,809,695 A | 3/1989 | Gwathmey et al. | |
| 4,896,661 A | 1/1990 | Bogert et al. | |
| 5,014,407 A | 5/1991 | Boughten et al. | |
| 5,020,519 A | 6/1991 | Hayes et al. | |
| D346,217 S | 4/1994 | Sparker | |
| 5,306,248 A * | 4/1994 | Barrington | 604/97.02 |
| 5,364,397 A | 11/1994 | Hayes et al. | |
| 5,391,170 A | 2/1995 | McGuire et al. | |
| 5,429,641 A | 7/1995 | Gotfried | |
| 5,484,440 A | 1/1996 | Allard | |
| 5,545,165 A | 8/1996 | Biedermann et al. | |
| 5,551,320 A | 9/1996 | Horobec et al. | |
| 5,616,143 A | 4/1997 | Schlapfer et al. | |
| 5,649,931 A | 7/1997 | Bryant et al. | |
| 5,672,175 A | 9/1997 | Martin | |
| 5,683,399 A | 11/1997 | Jones et al. | |
| 5,697,933 A | 12/1997 | Gundlapalli et al. | |
| 5,707,371 A | 1/1998 | Metz-Stavenhagen | |
| 5,720,751 A | 2/1998 | Jackson | |
| 5,725,532 A | 3/1998 | Shoemaker | |
| 5,746,757 A | 5/1998 | McGuire | |
| 5,782,831 A | 7/1998 | Sherman et al. | |
| 5,810,878 A | 9/1998 | Burel et al. | |
| 5,910,141 A | 6/1999 | Morrison et al. | |
| 5,941,885 A * | 8/1999 | Jackson | 606/104 |
| 5,951,564 A | 9/1999 | Schroder et al. | |
| 5,951,579 A | 9/1999 | Dykes | |
| 6,010,509 A | 1/2000 | Delgado et al. | |
| 6,036,692 A | 3/2000 | Burel et al. | |
| 6,099,528 A | 8/2000 | Saurat et al. | |
| 6,123,707 A | 9/2000 | Wagner | |
| 6,139,549 A | 10/2000 | Keller | |
| 6,183,472 B1 | 2/2001 | Lutz et al. | |
| 6,210,330 B1 | 4/2001 | Tepper et al. | |
| 6,251,112 B1 | 6/2001 | Jackson | |
| 6,258,090 B1 | 7/2001 | Jackson | |
| 6,371,973 B1 | 4/2002 | Tepper et al. | |
| 6,440,133 B1 | 8/2002 | Beale et al. | |
| 6,440,142 B1 | 8/2002 | Ralph et al. | |
| 6,440,144 B1 | 8/2002 | Bacher | |
| 6,511,484 B2 | 1/2003 | Torode et al. | |
| 6,530,929 B1 | 3/2003 | Justis et al. | |
| 6,589,249 B2 | 7/2003 | Sater et al. | |
| 6,648,888 B1 | 11/2003 | Shluzas | |
| 6,660,006 B2 | 12/2003 | Markworth et al. | |
| 6,726,692 B2 | 4/2004 | Bette et al. | |
| 6,743,231 B1 | 6/2004 | Gray et al. | |
| 6,746,449 B2 | 6/2004 | Jones et al. | |
| 6,752,832 B2 | 6/2004 | Neumann | |
| 6,755,829 B1 | 6/2004 | Bono et al. | |
| 6,790,208 B2 | 9/2004 | Oribe et al. | |
| 6,790,209 B2 | 9/2004 | Beale et al. | |
| 6,827,722 B1 | 12/2004 | Schoenefeld | |
| 7,083,621 B2 | 8/2006 | Shaolian et al. | |
| 7,156,849 B2 | 1/2007 | Dunbar et al. | |
| 7,179,254 B2 | 2/2007 | Pendekanti et al. | |
| 7,179,261 B2 | 2/2007 | Sicvol et al. | |
| 7,278,995 B2 | 10/2007 | Nichols et al. | |
| 7,320,689 B2 | 1/2008 | Keller | |
| 7,371,239 B2 | 5/2008 | Dec et al. | |
| 7,462,182 B2 | 12/2008 | Lim | |
| 7,485,120 B2 | 2/2009 | Ray | |
| 7,491,207 B2 | 2/2009 | Keyer et al. | |
| 7,527,638 B2 | 5/2009 | Anderson et al. | |
| 7,572,281 B2 | 8/2009 | Runco et al. | |
| 7,621,918 B2 * | 11/2009 | Jackson | 606/86 A |
| 7,651,502 B2 * | 1/2010 | Jackson | 606/99 |
| 7,666,188 B2 | 2/2010 | Anderson et al. | |
| 7,708,763 B2 | 5/2010 | Selover et al. | |
| 2001/0029376 A1 | 10/2001 | Sater et al. | |
| 2002/0095153 A1 | 7/2002 | Jones et al. | |
| 2003/0009168 A1 | 1/2003 | Beale et al. | |
| 2003/0028195 A1 | 2/2003 | Bette | |
| 2003/0083747 A1 | 5/2003 | Winterbottom et al. | |
| 2003/0125750 A1 | 7/2003 | Zwirnmann et al. | |
| 2003/0149438 A1 | 8/2003 | Nichols et al. | |
| 2003/0191370 A1 | 10/2003 | Phillips | |
| 2003/0199872 A1 | 10/2003 | Markworth et al. | |
| 2003/0225408 A1 | 12/2003 | Nichols et al. | |
| 2004/0049191 A1 | 3/2004 | Markworth et al. | |
| 2004/0147936 A1 | 7/2004 | Rosenberg et al. | |
| 2004/0147937 A1 | 7/2004 | Dunbar et al. | |
| 2004/0172057 A1 | 9/2004 | Guillebon et al. | |
| 2004/0176779 A1 | 9/2004 | Casutt et al. | |
| 2004/0220567 A1 | 11/2004 | Eisermann et al. | |
| 2004/0254576 A1 | 12/2004 | Dunbar et al. | |
| 2004/0267275 A1 | 12/2004 | Cournoyer et al. | |
| 2005/0015095 A1 | 1/2005 | Keller | |
| 2005/0033299 A1 | 2/2005 | Shluzas | |
| 2005/0055031 A1 | 3/2005 | Lim | |
| 2005/0059969 A1 | 3/2005 | McKinley | |
| 2005/0079909 A1 | 4/2005 | Singhaseni | |
| 2005/0090824 A1 | 4/2005 | Shluzas et al. | |
| 2005/0131408 A1 | 6/2005 | Sicvol et al. | |
| 2005/0131420 A1 | 6/2005 | Techiera et al. | |
| 2005/0131421 A1 | 6/2005 | Anderson et al. | |
| 2005/0131422 A1 | 6/2005 | Anderson et al. | |
| 2005/0143749 A1 | 6/2005 | Zalenski et al. | |
| 2005/0149036 A1 | 7/2005 | Varieur et al. | |
| 2005/0149048 A1 | 7/2005 | Leport et al. | |
| 2005/0149053 A1 | 7/2005 | Varieur et al. | |
| 2005/0192570 A1 | 9/2005 | Jackson | |
| 2005/0192579 A1 | 9/2005 | Jackson | |
| 2005/0228392 A1 | 10/2005 | Keyer et al. | |
| 2005/0261702 A1 | 11/2005 | Oribe et al. | |
| 2006/0009775 A1 | 1/2006 | Dec et al. | |
| 2006/0025768 A1 | 2/2006 | Iott et al. | |
| 2006/0036254 A1 | 2/2006 | Lim | |
| 2006/0036260 A1 | 2/2006 | Runco et al. | |
| 2006/0069391 A1 | 3/2006 | Jackson | |
| 2006/0074418 A1 | 4/2006 | Jackson | |
| 2006/0079909 A1 | 4/2006 | Runco et al. | |
| 2006/0089651 A1 | 4/2006 | Trudeau et al. | |
| 2006/0095035 A1 | 5/2006 | Jones et al. | |
| 2006/0111712 A1 | 5/2006 | Jackson | |
| 2006/0111730 A1 | 5/2006 | Hay | |
| 2006/0111713 A1 | 6/2006 | Jackson | |
| 2006/0166534 A1 | 7/2006 | Brumfield et al. | |
| 2006/0166535 A1 | 7/2006 | Brumfield et al. | |
| 2006/0293692 A1 * | 12/2006 | Whipple et al. | 606/104 |
| 2007/0093849 A1 | 4/2007 | Jones et al. | |
| 2007/0129731 A1 | 6/2007 | Sicvol et al. | |
| 2007/0161998 A1 | 7/2007 | Whipple | |
| 2007/0167954 A1 | 7/2007 | Sicvol et al. | |
| 2007/0173831 A1 | 7/2007 | Abdou | |
| 2007/0185375 A1 * | 8/2007 | Stad et al. | 600/101 |
| 2007/0213722 A1 | 9/2007 | Jones et al. | |
| 2007/0233097 A1 | 10/2007 | Anderson et al. | |
| 2007/0260261 A1 | 11/2007 | Runco et al. | |
| 2007/0270880 A1 * | 11/2007 | Lindemann et al. | 606/104 |
| 2008/0077134 A1 | 3/2008 | Dziedzic et al. | |
| 2008/0077135 A1 | 3/2008 | Stad et al. | |
| 2008/0243190 A1 | 10/2008 | Dziedzic et al. | |
| 2008/0255574 A1 | 10/2008 | Dye | |
| 2009/0030419 A1 | 1/2009 | Runco et al. | |
| 2009/0030420 A1 | 1/2009 | Runco et al. | |
| 2009/0054902 A1 | 2/2009 | Mickiewicz et al. | |
| 2009/0082811 A1 | 3/2009 | Stad et al. | |
| 2009/0088764 A1 | 4/2009 | Stad et al. | |
| 2009/0138056 A1 | 5/2009 | Anderson et al. | |
| 2009/0143828 A1 | 6/2009 | Stad et al. | |
| 2010/0137915 A1 | 6/2010 | Anderson et al. | |
| 2011/0144695 A1 | 6/2011 | Rosenberg | |

FOREIGN PATENT DOCUMENTS

| | | |
|---|---|---|
| DE | 29806563 U1 | 6/1998 |
| EP | 948939 A2 | 10/1999 |
| EP | 1574175 | 9/2005 |

| EP | 1648320 | | 4/2006 |
| --- | --- | --- | --- |
| EP | 1796564 | | 6/2007 |
| FR | 2680314 | | 2/1993 |
| FR | 2677242 | A1 | 7/1996 |
| FR | 2729291 | A1 | 7/1996 |
| WO | 9621396 | A1 | 7/1996 |
| WO | 2005006948 | A2 | 1/2005 |
| WO | 2006020443 | A1 | 2/2006 |

OTHER PUBLICATIONS

U.S. Patent No. 6,790,209 Reissue Application Declaration and related Transmittal Letter and Information Disclosure Statement citing schematic drawings from Sofamor, "Introducteur—Contreur De Tige", Jan. 1, 1994.

* cited by examiner

FIG. 8A
FIG. 8B
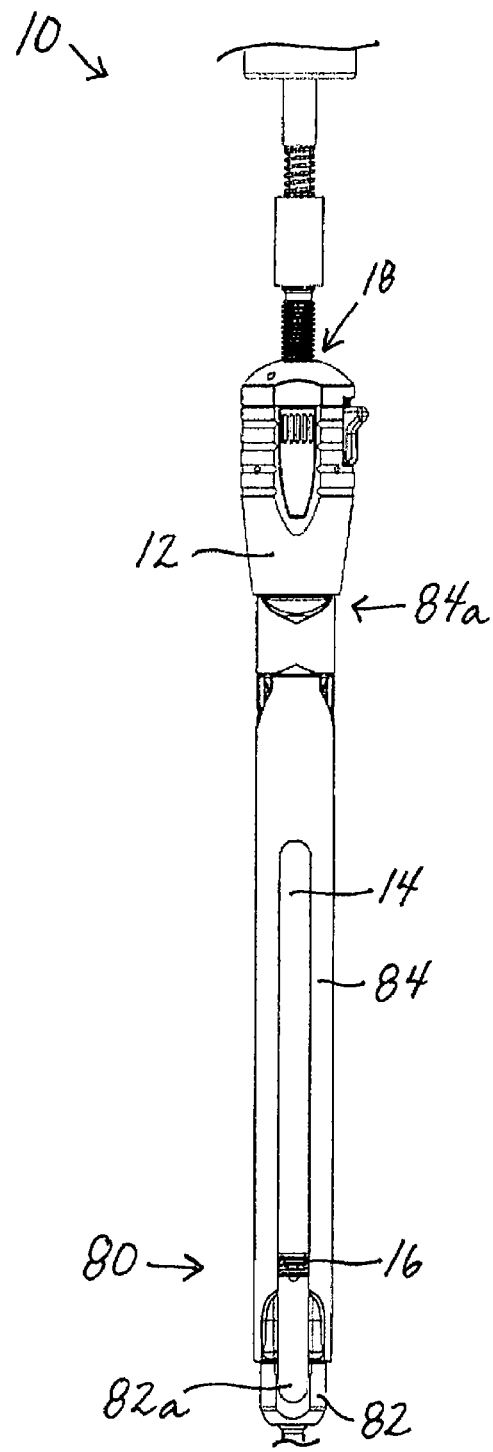
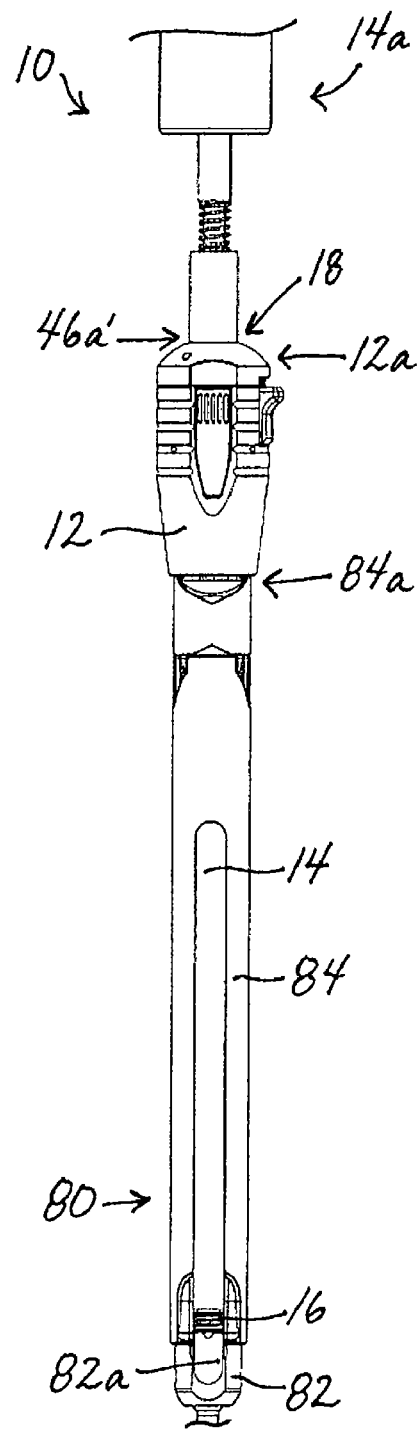

IN-LINE ROD REDUCTION DEVICE AND METHODS

FIELD OF THE INVENTION

The present invention relates to methods and devices for use in spinal surgery, and in particular to rod reduction devices and methods for using the same.

BACKGROUND OF THE INVENTION

Spinal fixation devices are used in orthopedic surgery to align and/or fix a desired relationship between adjacent vertebral bodies. Such devices typically include a spinal connector, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism, is used to lock the fixation rod into the rod-receiving head of the pedicle screw. In use, the shank portion of each screw is threaded into a vertebra, and once properly positioned, a fixation rod is seated through the rod-receiving member of each screw and the rod is locked in place by tightening a cap or other fastener mechanism to securely interconnect each screw and the fixation rod.

While current spinal fixation systems have proven effective, one challenge associated with such systems is mounting the fixation rods into the rod-receiving member of various fixation devices. In particular, it can be difficult to align and seat the rod into the rod receiving portion of adjacent fixation devices due to the positioning and rigidity of the vertebra into which the fixation device is mounted. Thus, the use of a spinal rod reduction device, also sometimes referred to as a spinal rod approximator, is often required in order to grasp the head of the fixation device and reduce the rod into the rod-receiving head of the fixation device.

While several rod reduction devices are known in the art, some tend to be bulky and cumbersome to use. Accordingly, there is a need for improved rod reduction devices and methods for seating a spinal rod in a rod-receiving member of one or more spinal anchors.

SUMMARY OF THE INVENTION

The present invention provides methods and devices for placing a spinal fixation rod into a rod receiving opening in a spinal anchor and installing a fastener to secure the rod to the spinal anchor. In one embodiment, the system can include a cap having a bore extending therethrough, an elongate drive rod that is adapted to extend through the bore, and a fastener that is disposed on a distal portion of the drive rod. The cap can include a mating element that is disposed on a distal end thereof and adapted to removably mate the cap to a spinal anchor or extension member that extends therefrom. In one embodiment, the mating element can be adapted to removably mate the cap to a screw extension that extends proximally from a spinal anchor and provides access to the rod receiving opening in the anchor. The cap can also include a driving element that is adapted to cooperate with a complementary driving element disposed on the rod to form a driving mechanism. Actuation of the driver mechanism can be effective to advance the drive rod through the cap to thereby reduce a spinal rod into a rod receiving opening of the spinal anchor and install the fastener to secure the rod to the spinal anchor.

In one embodiment, the driving element on the cap can include threads formed in at least a portion of the bore. For example, the driving element of the cap can be a threaded member that has at least a partial thread formed in at least a portion of the bore that extends through the cap. The threaded member can be selectively engageable in (1) a drive rod configuration in which the partial thread is engaged with the drive rod to permit longitudinal translation of the rod upon rotation of the rod and (2) a translation configuration in which the threaded member is disengaged from the threads on the rod to permit longitudinal translation of the rod upon translation of the rod without rotation of the rod. In an exemplary embodiment, the threaded member can be pivotably disposed in the cap such that it can pivot between engaged and disengaged positions. The driver mechanism can also include a locking mechanism that is adapted to secure the driver mechanism in the drive rod configuration.

As indicated above, the drive rod of the system can also include a driving element. In one embodiment, the driving element on the drive rod can include threads that are formed on a proximal portion thereof and are adapted to engage the threads formed in the bore of the cap. The threads on the drive rod can be timed with threads formed on the fastener to prevent misalignment or cross threading of the fastener. The drive rod can also include a clutch mechanism that is disposed on a proximal portion thereof. In one embodiment, the clutch can be adapted disengage the driving element of the drive rod to allow the fastener to align with the rod-receiving opening of the spinal implant once the threads of the fastener have engaged or are about to engage the opening. In another embodiment, the clutch can be adapted to disengage a handle portion of the rod from a driver portion of the rod to prevent over-rotation and over-tightening of the fastener.

The drive rod can also include a fastener-retaining member and a reduction tip. The fastener-retaining member can be formed on a distal portion thereof, and, in one embodiment, can be a spring tip having a square or round cross-section. Other exemplary embodiments of the fastener-retaining member include, for example, a split tip and a cam tip. The reduction tip can be disposed distal to a fastener that is retained by the fastener-retaining member and can be adapted to reduce a rod into a rod-receiving opening of a spinal anchor. In one embodiment, the reduction tip can be spring loaded such that it can retract to allow the fastener retained by the fastener-retaining member to fully seat into a rod-receiving opening of a spinal anchor. The reduction tip can also be pivotably coupled to the drive rod and be adapted to remain stationary while the drive rod is rotated with respect to the cap.

Methods for reducing a rod into a rod-receiving opening of a spinal anchor are also provided. In one embodiment, the method can include mating an extension member to a spinal anchor, advancing a spinal rod through the extension member to position the spinal rod in relation to the spinal anchor, mating a cap of a rod reduction system to a proximal end of the extension member, and engaging the cap with a drive rod of the reduction system to thereby reduce and fasten the spinal rod into a rod-receiving opening of the spinal anchor. In an exemplary embodiment, engaging the cap can include inserting the drive rod through a bore that extends through the cap and rotating the drive rod with respect to the cap to advance the drive rod through the cap and extension member to thereby reduce and fasten a spinal rod into a rod-receiving opening of the spinal anchor. A fastener can be secured to the drive rod once the rod is through the bore in the cap or the drive rod can include a pre-loaded fastener. Engaging the cap can also include establishing a threaded connection between a portion of the drive rod and a portion of the cap to enable longitudinal translation of the drive rod upon rotation of the drive rod and rotating the drive rod with respect to the cap to advance the drive rod through the cap and extension member. In yet another embodiment, the method can also include engaging a spinal anchor with a reduction tip that is disposed on the drive rod at a position that is distal to a fastener-retaining member of the drive rod.

BRIEF DESCRIPTION OF THE DRAWINGS

The invention will be more fully understood from the following detailed description taken in conjunction with the accompanying drawings, in which:

FIG. 8A is a perspective view of the rod reduction system shown in FIG. 1 showing the system mated to an extension member that extends proximally from a spinal anchor and the drive rod being advanced through the extension member;

FIG. 8B is another perspective view of the rod reduction system shown in FIG. 1 showing the drive rod of the system further advanced through the extension member;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides methods and devices for placing a spinal fixation rod into a rod receiving opening in a spinal anchor and installing a fastener to secure the rod to the spinal anchor. In general, a rod reduction system is provided that can removably mate to a spinal anchor and be effective to reduce and fasten a rod disposed within or adjacent to a rod receiving opening of the anchor. While the reduction system is described herein as being mated to a spinal anchor, one skilled in the art will appreciate that the reduction system can be removably mated to a spinal anchor, an extension member that is mated to or integrally formed with a spinal anchor, or any other spinal anchor and extension configuration. One skilled in the art will also appreciate that although the system is described primarily in connection with spinal applications, the system may be used to engage any type of bone anchor or other implant and/or to position any type of fixation element relative to a bone anchor.

Figure 1:
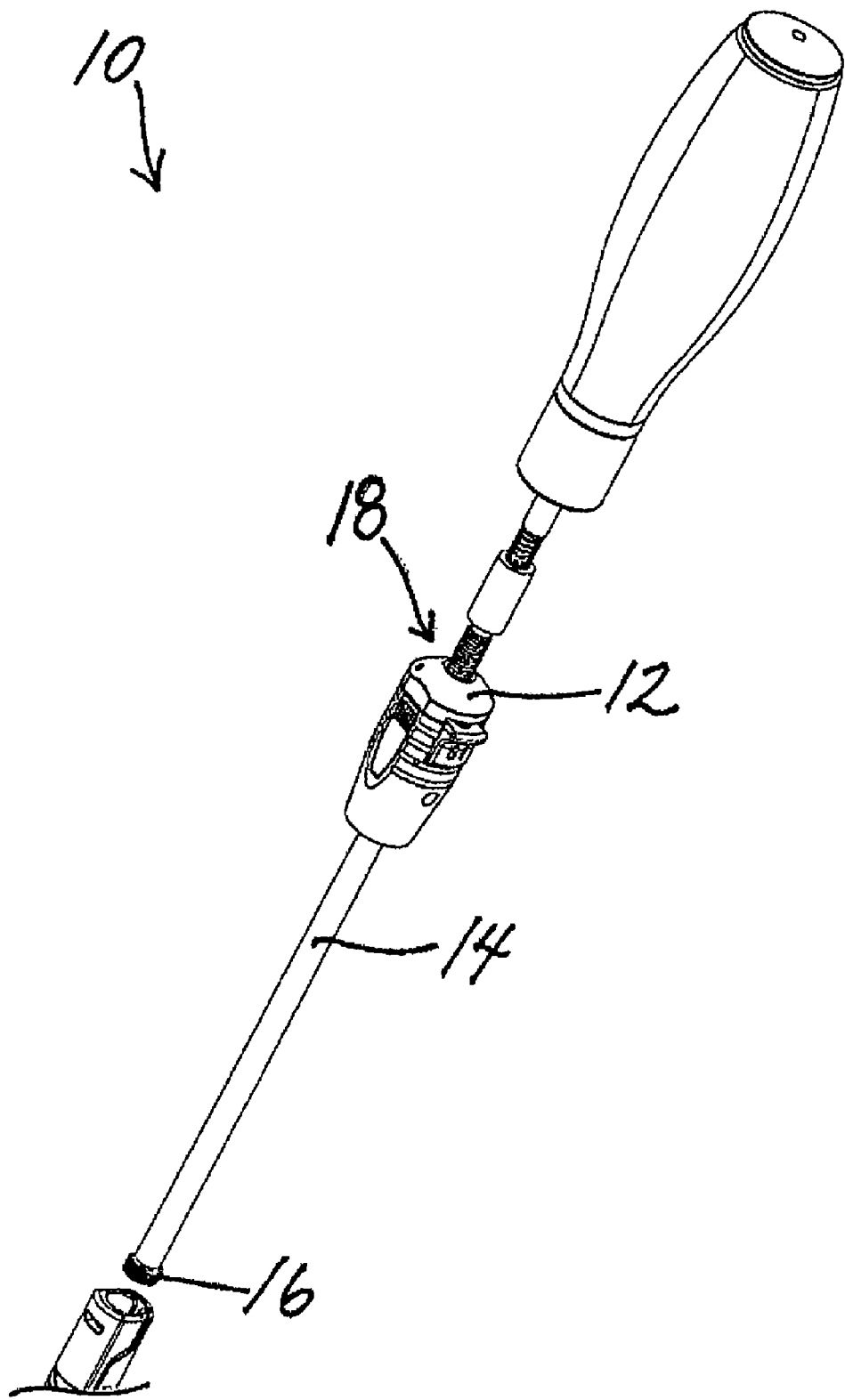
FIG. 1 is a perspective view of a rod reduction system according to one embodiment of the present invention.

FIG. 1 illustrates one exemplary embodiment of a rod reduction system 10 in accordance with the present invention. As shown, the rod reduction system 10 generally includes a cap 12 having a bore 18 extending therethrough and an elongate drive rod 14 that is adapted to extend through the bore 18 and includes a fastener 16 disposed at a distal portion thereof for securing a spinal rod to a spinal anchor. Actuation of the drive rod 14 with respect to the cap 12 can be effective to advance the drive rod 14 through the cap 12 to thereby reduce a spinal rod into a rod receiving opening of a spinal anchor and install the fastener 16 to secure the rod to the spinal anchor.

Figure 2:
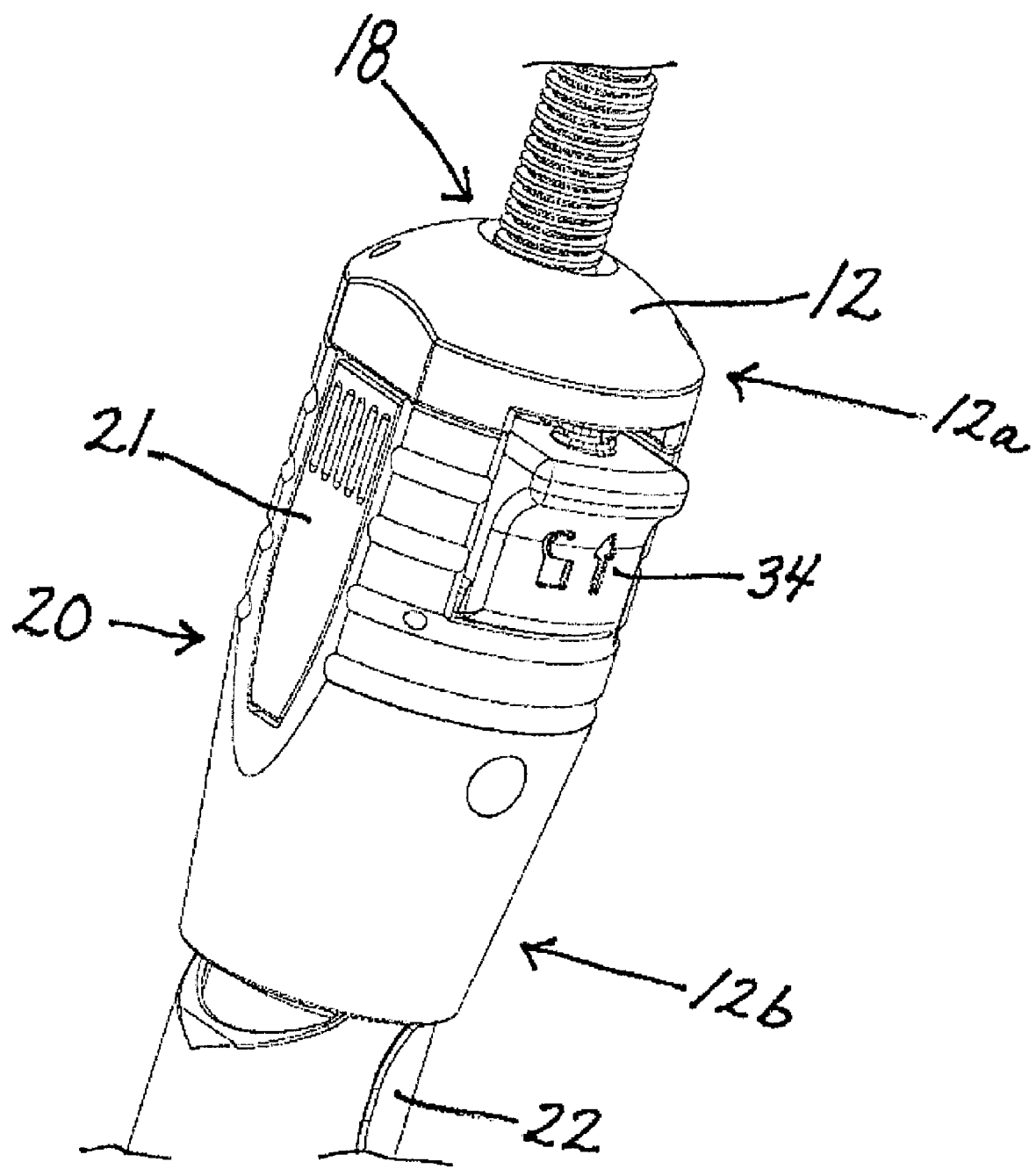
FIG. 2 is an enlarged perspective view of the cap of the rod reduction system shown in FIG. 1.
Figure 3B:
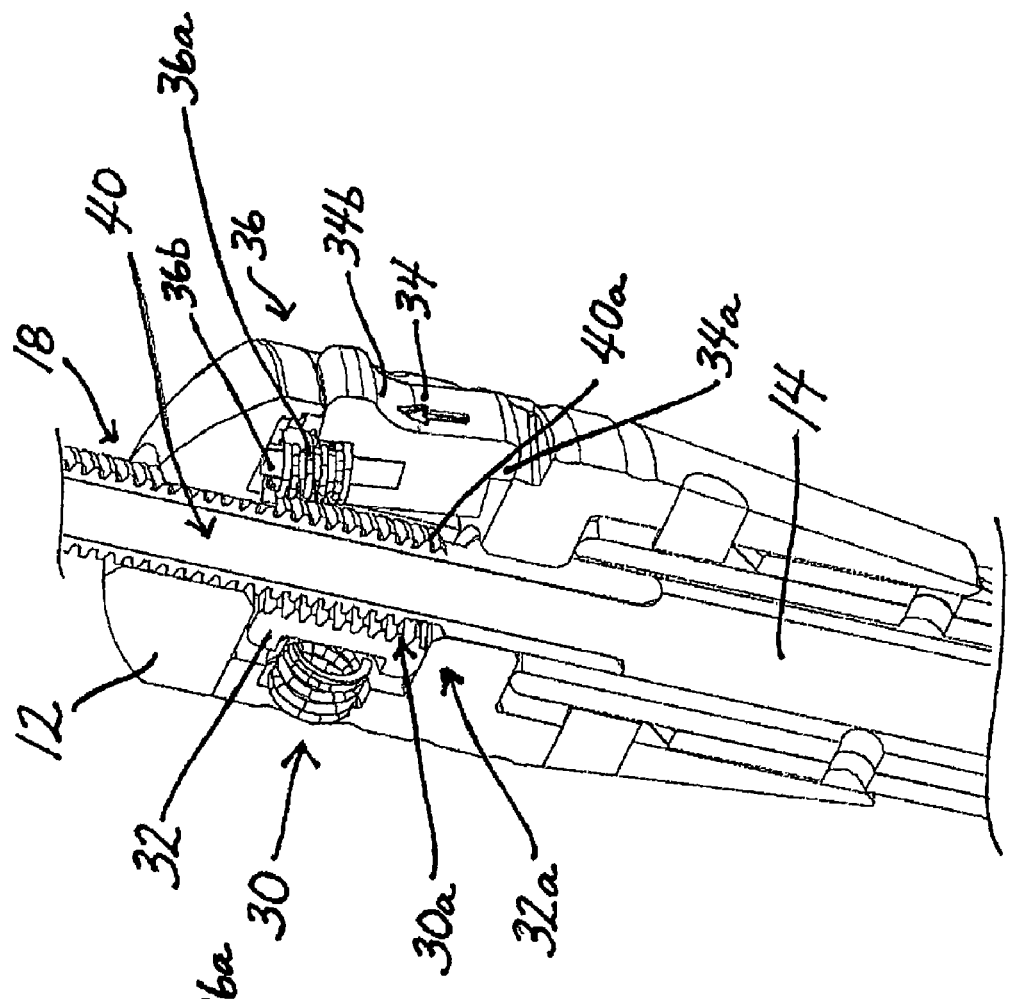
FIG. 3B is a cross-sectional view of the cap shown in FIG. 2 showing the threads on the cap disengaged from the threads on the drive rod.
Figure 9:
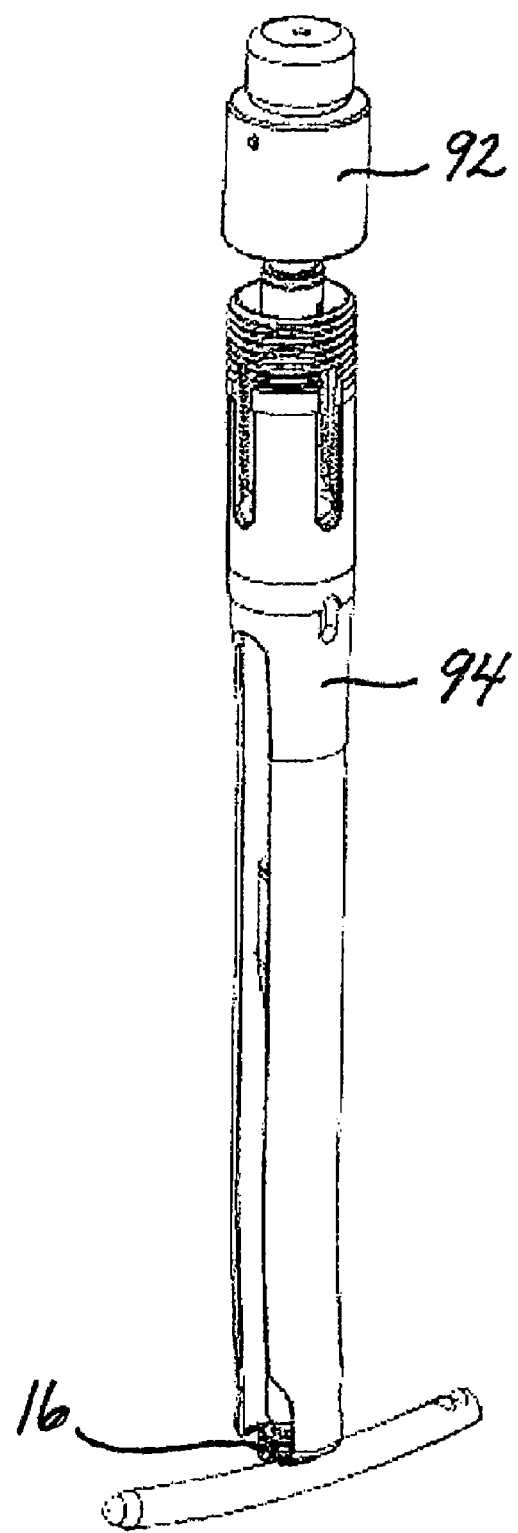
FIG. 9 is a perspective view of a rod reduction system according to one embodiment of the present invention.
Figure 10:
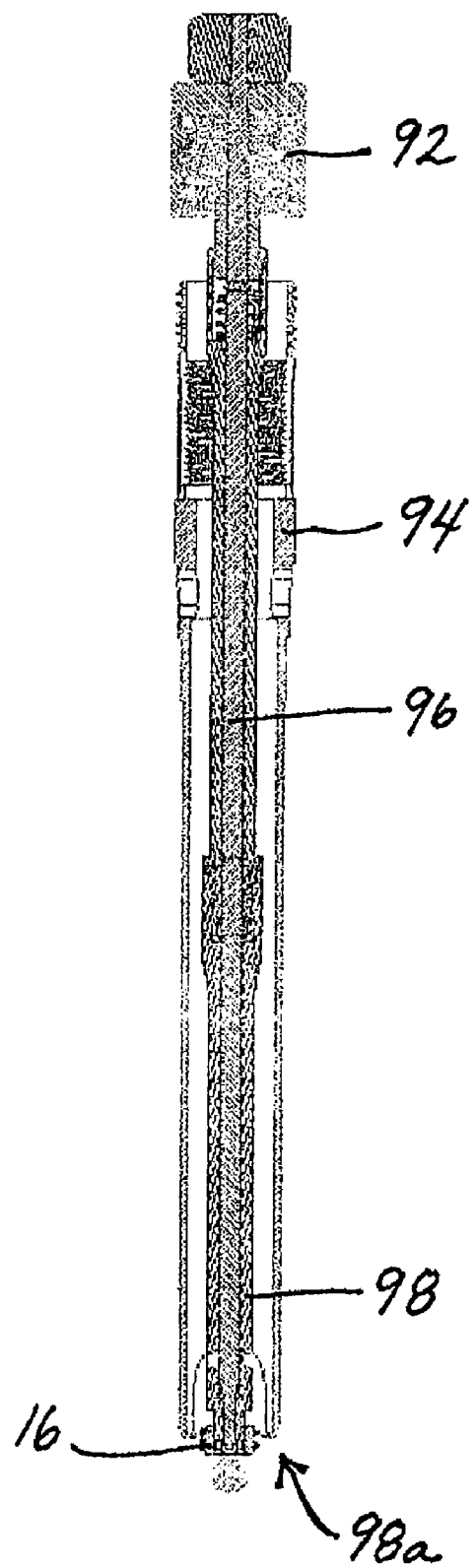
FIG. 10 is a cross-sectional view of the rod reduction system shown in FIG. 9.

The cap 12, which is shown in more detail in FIGS. 2-3B, can have a variety of configurations. In an exemplary embodiment, as shown, the cap 12 is a generally cylindrical body having a bore 18 extending therethrough, a mating element 20, and a driving element 30. The mating element 20 can be disposed on a distal end 12*b* thereof and be adapted to removably mate the cap 12 to a spinal anchor. While various configurations are available for the mating element 20, in an exemplary embodiment, shown in FIGS. 2-3B, the mating element 20 includes a pawl (not shown) that is disposed within the bore 18 of the cap 12. The pawl can be configured to mate to or fit into a groove (not shown) formed in a proximal portion of a spinal anchor such that the cap 12 can snap onto the spinal anchor. The pawl can also be associated with a lever 21 that is disposed on an outer portion of the cap 12 and is adapted to disengage the pawl from the groove and thereby release the cap 12 from the spinal anchor. Although the mating element 20 is described as a single pawl and groove configuration, one skilled in the art will appreciate that the mating element 20 can include any number of pawls disposed in a variety of configurations. Other techniques for mating the cap 12 to a spinal anchor include, for example, a ball and plunger configuration and a cap 12 that can threadably engage a spinal anchor. For example, FIGS. 9-10 illustrate an exemplary embodiment showing a cap 92 that is threadably mated to an extension member 94 that extends proximally from a spinal anchor (not shown).

Various configurations are available for the driving element 30 of the cap 12. In an exemplary embodiment, shown in FIGS. 3A-3B, the driving element 30 includes threads 30a formed in a portion of the bore 18 extending through the cap 12. The threads 30a can be configured to cooperate with a complementary driving element 40 formed on the elongate drive rod 14 of the rod reduction system 10 which is described below in detail. As shown, the driving element 30 of the cap 12 includes a mechanism that enables the threads 30a of the driving element 30 to be selectively engaged or disengaged from the drive rod 14. When the threads are engaged, the drive rod 14 can move in the axial direction only as a result of rotation of the drive rod 14. When the threads are disengaged, forward or rearward movement (i.e., linear translation) of rod 14 can be effected without rotation.

Figure 3A:
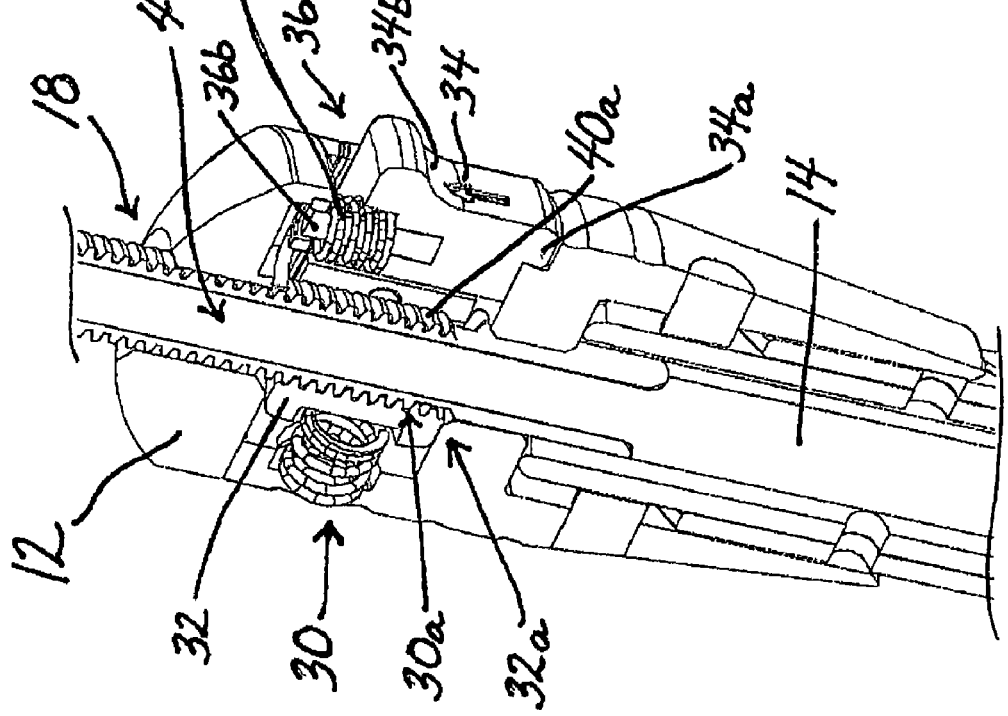
FIG. 3A is a cross-sectional view of the cap shown in FIG. 2 showing the threads on the cap engaged with the threads on the drive rod.

As shown in FIGS. 3A-3B, the cap 12 includes a female threaded member 32 that is a half nut located in a hemicylindrical groove 32a in the cap 12 and is aligned with the bore 18. The female threaded member 32 has threads 30a formed on at least a portion thereof. The threads 30a are complementary to and adapted to mate with the threads 40a on the drive rod 14. In one embodiment, the half nut 32 can be biased to a joined position such that the threads 30a in the groove 32a are in mating contact with the threads 40a on the drive rod 14. This configuration enables longitudinal translation of the rod 14 upon rotation of the rod 14. In this embodiment, the cap 12 can include a release mechanism 34 that is adapted to separate the half nut 32 from the drive rod 14 such that the threads 30a on the half nut 32 are unable to mate with the threads 40a on the drive rod 14. By disengaging the threads 30a in the groove 32a from the threads 40a on the drive rod 14, longitudinal translation of the drive rod 14 without rotation of the rod 14 is permitted. The release mechanism 34 can be disposed on the cap 12 and can include a button, switch or other mechanism to trigger the separation of the threads 30a on the half nut 32 from the threads 40a on the drive rod 14.

In another embodiment (not shown), the half nut can be biased to a separated position in which the threads in the groove are unable to mate with the threads on the drive rod allowing translation of the drive rod without rotation of the rod. In this embodiment, an engagement mechanism is adapted to urge the threads in the groove into mating contact with the threads on the drive rod enabling translation of the rod only upon rotation of the rod. Similar to the release mechanism, the engagement mechanism can be disposed on the cap and can include a button, switch or other mechanism to trigger the engagement of the threads of the half nut with the threads on the drive rod. Although the driving element is shown and described as a threaded member, one skilled in the art will appreciate that a variety of configurations are available for the driving element including, for example, ratchet and gear mechanisms.

The driving element 30 can also include a locking mechanism that is adapted to secure the half nut 32 in an engaged or disengaged configuration. In one exemplary embodiment, shown in FIGS. 3A-3B (showing a locked, engaged configuration and an unlocked, disengaged configuration, respectively), a locking mechanism 36 associated with the half nut 32 of the driving element 30 can include a spring 36a that is held in position by a stationary pin 36b. The spring 36a can be compressed such that it applies a constant downward force on the release mechanism 34. As the downward force is applied to the release mechanism 34, the release mechanism slides downward into the position illustrated in FIG. 3A. Once the locking portion 34a has cleared the sidewall of the cap 12, the release mechanism 34 is forced downward by the spring 36a and locked in place. The locking portion 34a can be adapted to fit against the sidewall of the cap 12, thereby holding the release mechanism 34 in place and maintaining the thread engagement. In this embodiment, the release mechanism 34 includes a locking portion 34a and a scalloped portion 34b. To disengage the threads 30a, 40a (as illustrated in FIG. 3B), a force can be applied to the scalloped portion 34b of the release mechanism 34 in an upward and inward direction, thereby unlocking the release mechanism 34 and urging the threads 30a of the half nut 32 away from the threads 40a on the drive rod 14.

Figure 13A:
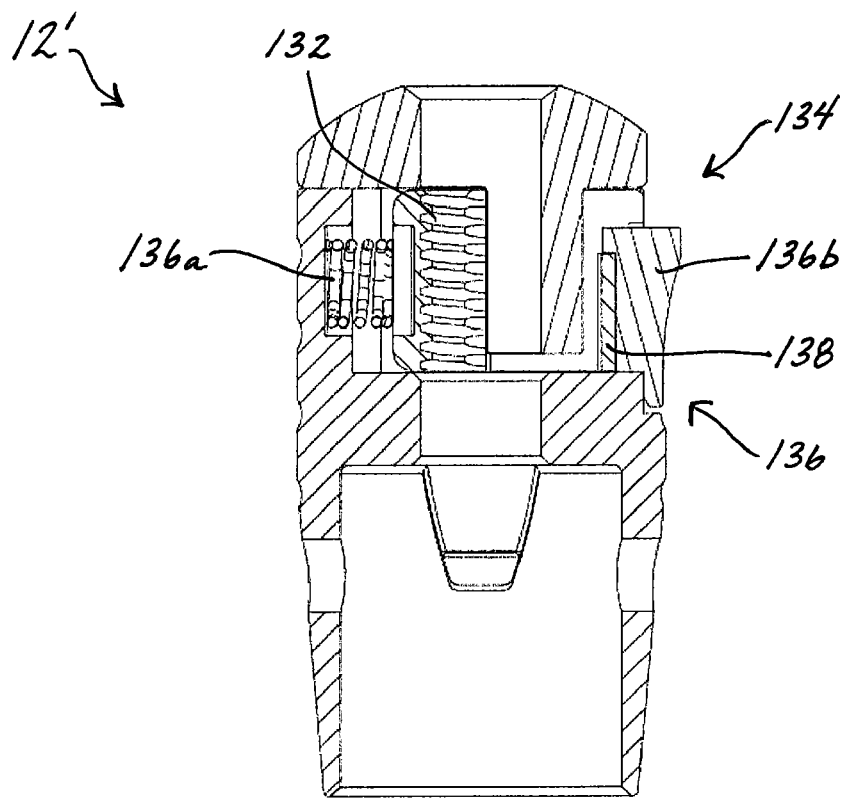
FIG. 13A is a cross-sectional view of one exemplary embodiment of a cap showing the threads on the cap in an engaged position.
Figure 13B:
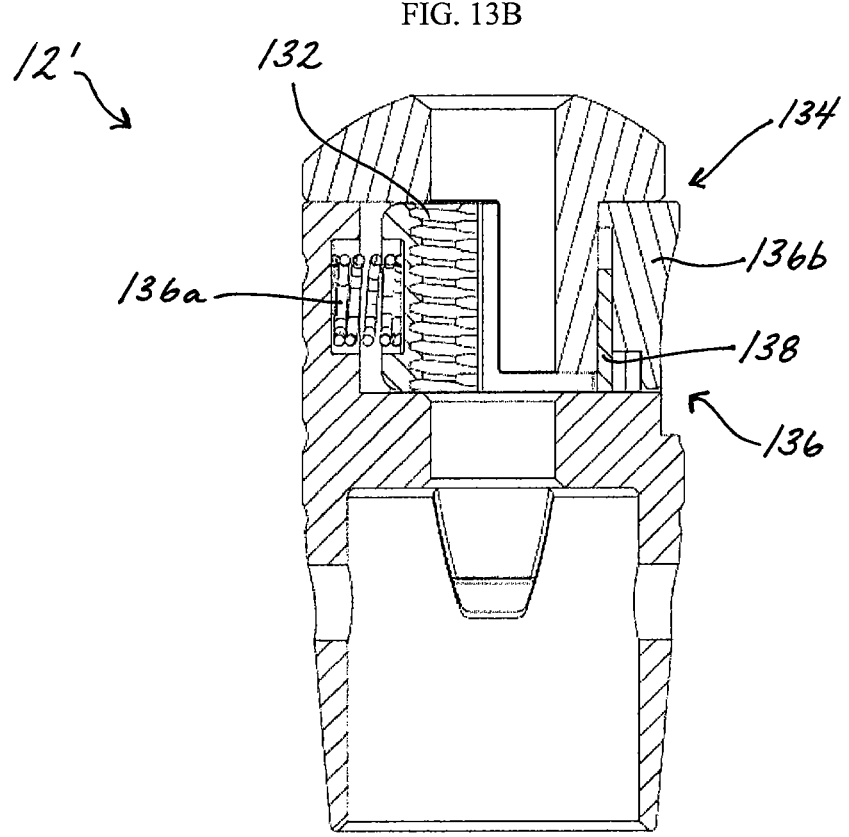
FIG. 13B is a cross-sectional view of the cap shown in FIG. 13A showing the threads on the cap in a disengaged position.

Another exemplary embodiment of a locking mechanism is shown in FIGS. 13A-13B (showing a locked, engaged configuration and an unlocked, disengaged configuration, respectively). In this embodiment, the release mechanism 134 can take the form of a button 138 and the locking mechanism 136 can include a spring 136a and a slider member 136b. As shown, the slider member 136b is slidably disposed in a channel formed in the button 138 of the release mechanism 134. The slider member 136b can be adapted to fit against the sidewall of the cap 12', thereby holding the release mechanism 134 in place and maintaining the thread engagement. The spring 136a can be compressed such that it applies a constant force on the half nut 132. To disengage the threads, the slider member 136b can be pushed upward or proximally with respect to the button 138 thereby unlocking the release mechanism 134. The button 138 can then be depressed to urge the threads of the half nut 132 away from the threads on the drive rod. As illustrated in FIGS. 13A-13B, the half nut 132 and button 138 are integrally formed as a single component; however, in another exemplary embodiment the half nut and button can be separate components (not shown). In another exemplary embodiment (not shown), the slider member 136b can be spring loaded in the down or locked position.

Figure 11:
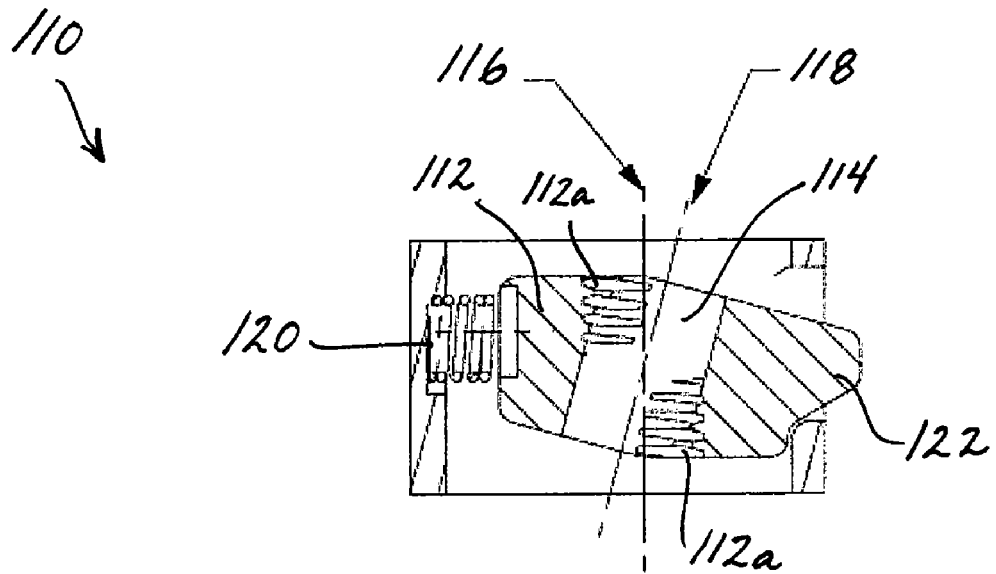
FIG. 11 is a cross-sectional view of one embodiment of the driving element of the cap shown in FIG. 2.
Figure 12:
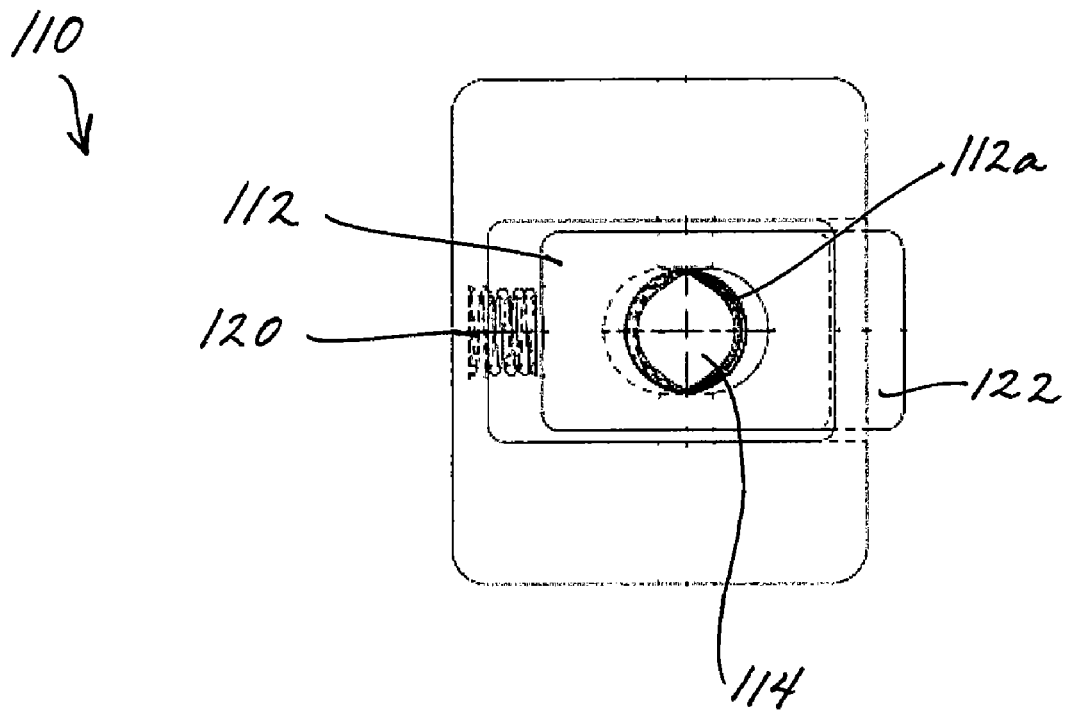
FIG. 12 is a top view of the driving element shown in FIG. 11.

Another exemplary embodiment of the driving element of the cap 12 is shown in FIGS. 11 and 12. Similar to the embodiment described above, the driving element 110 includes a threaded member 112 that is disposed in the bore 18 of the cap 12. The threaded member 112 can have threads 112a formed on at least a portion thereof that are complementary to and adapted to mate with the threads 40a on the drive rod 14. As shown in FIGS. 11 and 12, the threads 112a are formed in a bore 114 that extends through the threaded member 112. The bore 114 can be formed such that it has two axes. A first axis 116 or engagement axis 116 can be formed to allow the threaded member 112 to engage the drive rod 14, and a second axis 118 or disengagement axis 118 can be formed to allow the threaded member 112 to be disengaged from the drive rod 14. The threads 112a can be formed along the engagement axis 116. The threaded member 112 can be pivotably disposed in the cap 12 such that it can pivot between engaged and disengaged positions. As illustrated in FIGS. 11 and 12, the driving element 110 also includes a spring 120 that applies a force to the threaded member 112 and is adapted to maintain the engagement of the threaded member 112 with the drive rod 14. The driving element 110 can further include a release mechanism 122 that is adapted to pivot the threaded member 112 between engaged and disengaged positions. FIG. 11 shows the threaded member 112 in an engaged position. To disengage the threaded member 112 from the drive rod 14, a force can be applied to the release mechanism 122 in an upward direction, thereby pivoting the threaded member 112 and urging the threads 112a of the threaded member 112 away from the threads 40a on the drive rod 14. As with the above embodiment, by disengaging the threads 112a of the threaded member 112 from the threads 40a on the drive rod 14, longitudinal translation of the drive rod 14 without rotation of the rod 14 is permitted.

As indicated above, the rod reduction system 10 also includes an elongate drive rod 14 that is adapted to extend through the bore 18 in the cap 12 and includes a driving element 40 that cooperates with the driving element 30 of the cap 12 to form a driving mechanism. The drive rod 14, which is shown in more detail in FIGS. 4-6B, can have a variety of configurations. For example, as shown, the drive rod is a generally cylindrical elongate member having a driving element 40 formed on a proximal portion 14a thereof, a fastener-retaining member 42 formed on a distal portion 14b thereof, and a reduction tip 44 disposed distal to the fastener-retaining member 42.

Figure 4:
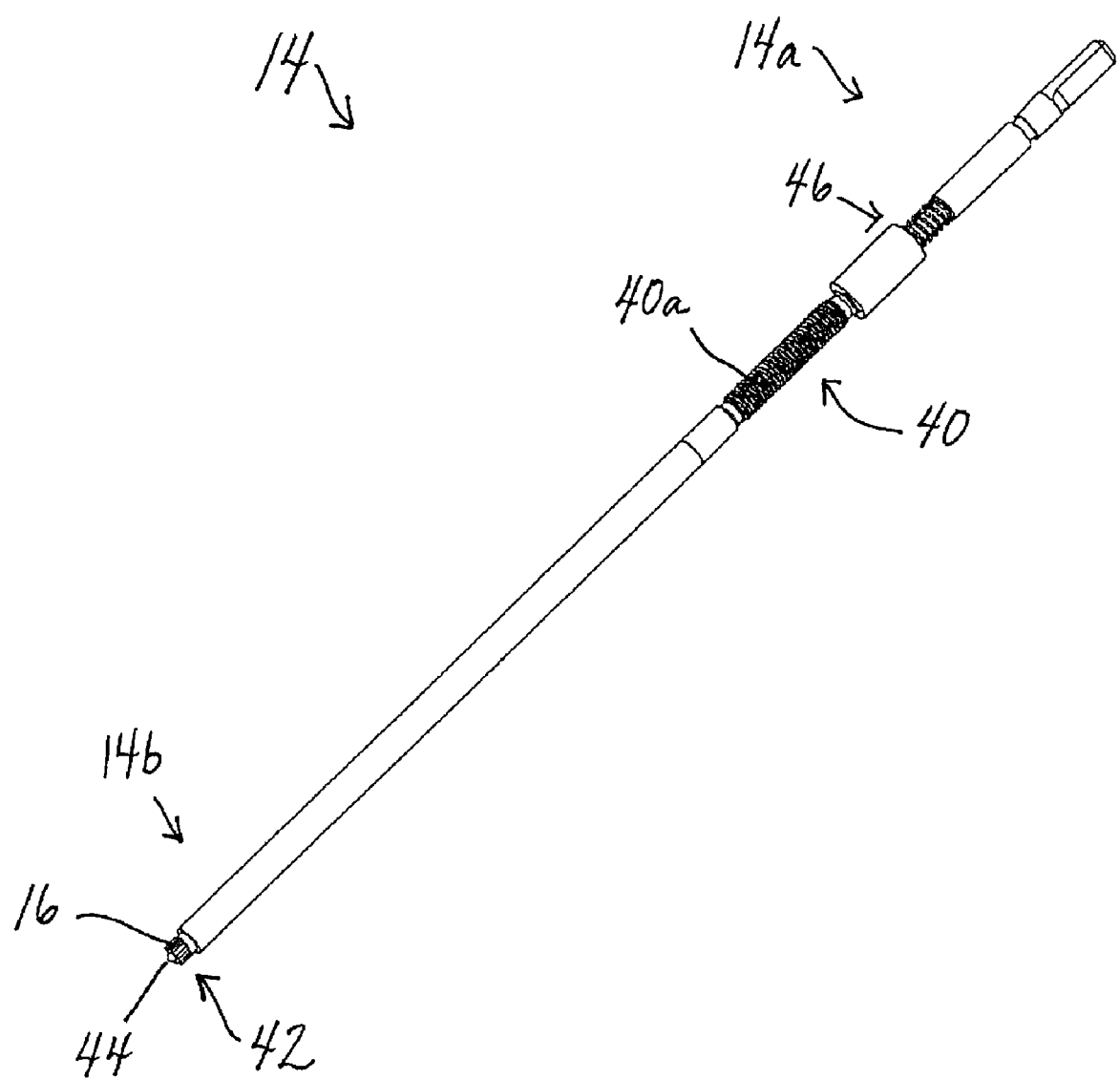
FIG. 4 is a perspective view of the drive rod of the rod reduction system shown in FIG. 1.

A variety of configurations are available for the driving element 40 of the drive rod 14. For example, as shown in FIGS. 3A-4, the driving element 40 includes a threaded portion 40a disposed on a proximal portion 14a of the drive rod 14 that is adapted to mate to threads 30a formed in the cap 12. As shown, the threaded portion 40a is a threaded sleeve that is disposed around a proximal portion 14a of the drive rod 14. In another embodiment (not shown), the threaded portion can be integrally formed with the drive rod 14. The threads 40a formed on the drive rod 14 can be configured such that rotation of the drive rod 14 with respect to the cap 12 can be effective to advance the drive rod 14 through the cap 12. Although the driving element 40 is shown and described as threads 40a disposed on a proximal portion 14a of the drive rod 14, one skilled in the art will appreciate that the driving element 40 can be a ratchet, gear, or other mechanism that is adapted to cooperate with a complementary driving element disposed in the cap 12.

Figure 6B:
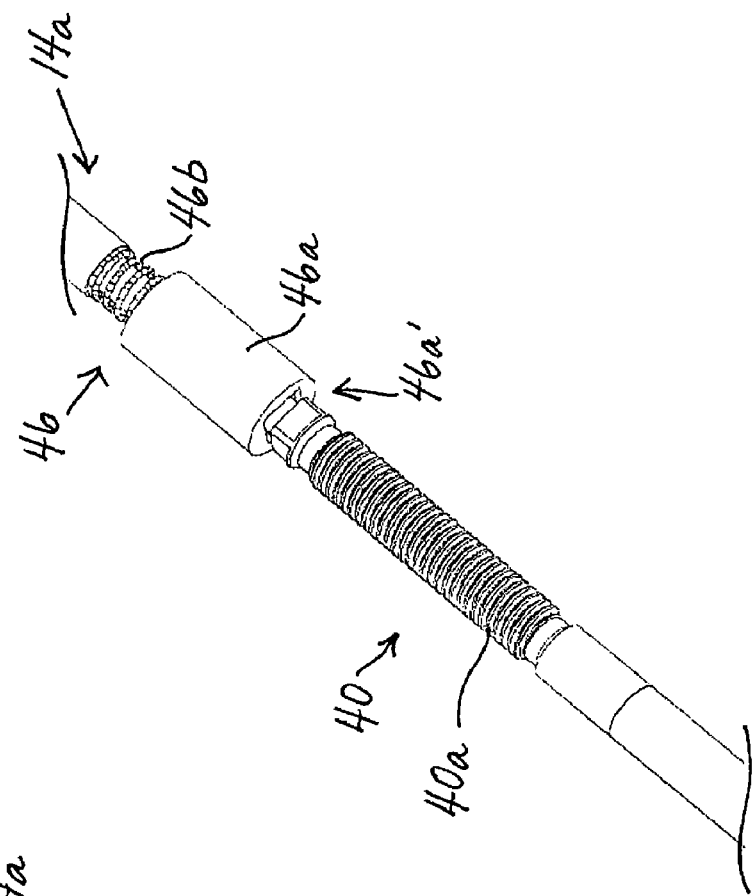
FIG. 6B is a perspective view of a portion of the drive rod of the rod reduction system shown in FIG. 1 showing a handle portion of the drive rod disengaged from a driver portion of the drive rod.
Figure 6A:
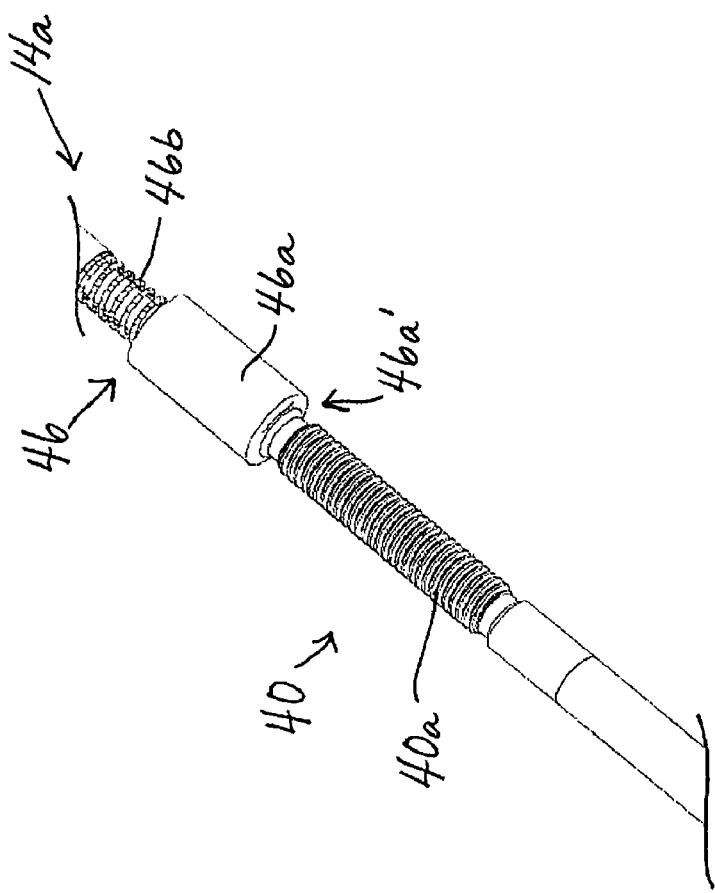
FIG. 6A is a perspective view of a portion of the drive rod of the rod reduction system shown in FIG. 1 showing the clutch of the drive rod.

The driving element 40 can also be associated with a clutch 46 that is disposed on a proximal portion 14a of the drive rod 14. In general, the clutch 46 can be adapted to disengage the driving element of the drive rod 14 from the rod 14 to allow the fastener 16 to align with the rod-receiving opening of the spinal anchor. For example, in an exemplary embodiment, shown in FIGS. 6A-6B, the threaded portion 40a is mated to the drive rod 14 by interference fit and the clutch 46 includes a spring loaded stop member 46a that is disposed proximal to the threaded portion 40a. As the drive rod 14 is advanced through the cap 12, a distal end 46a' of the stop member 46a can abut a proximal end of the cap 12. Continued advancement of the drive rod 14 can be effective to overcome the biasing force of the spring 46b and push the stop member 46a toward the proximal end 14a of the drive 14. As shown in FIG. 6B, proximal movement of the stop member 46a is effective to disengage the threaded portion 40a from the drive rod 14. Disengaging the threaded portion 40a from the drive rod 14 can enable free rotation and translation of the drive rod 14 with respect to the cap 12 and thereby allow the fastener 16 to be aligned with the rod-receiving opening of the spinal implant. In another exemplary embodiment (not shown), the threaded portion can be integrally formed with the drive rod and the spring-loaded clutch can be adapted to disengage a handle portion of the drive rod from a driver portion of the rod to prevent over-rotation of the drive rod and over-tightening of the fastener. In this embodiment, the driver portion of the drive rod can be mated to the handle portion of the rod by interference fit. As with the above embodiment, the clutch can include a spring loaded stop member that is disposed on a distal end of the handle portion of the drive rod and can abut a proximal end of the cap as the drive rod is advanced therethrough. Continued advancement of the drive rod can be effective to overcome the biasing force of the spring and push the stop member toward the proximal end of the handle portion of the drive rod, thereby disengaging the handle portion of the drive rod from the driver portion of the rod and preventing over-rotation and/or over-tightening.

Figure 5B:
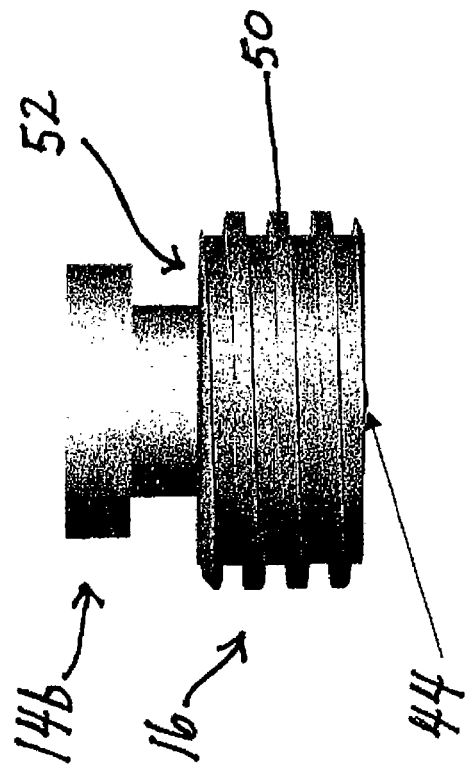
FIG. 5B is a perspective view of the distal end of the drive rod of the rod reduction system shown in FIG. 5A.
Figure 5A:
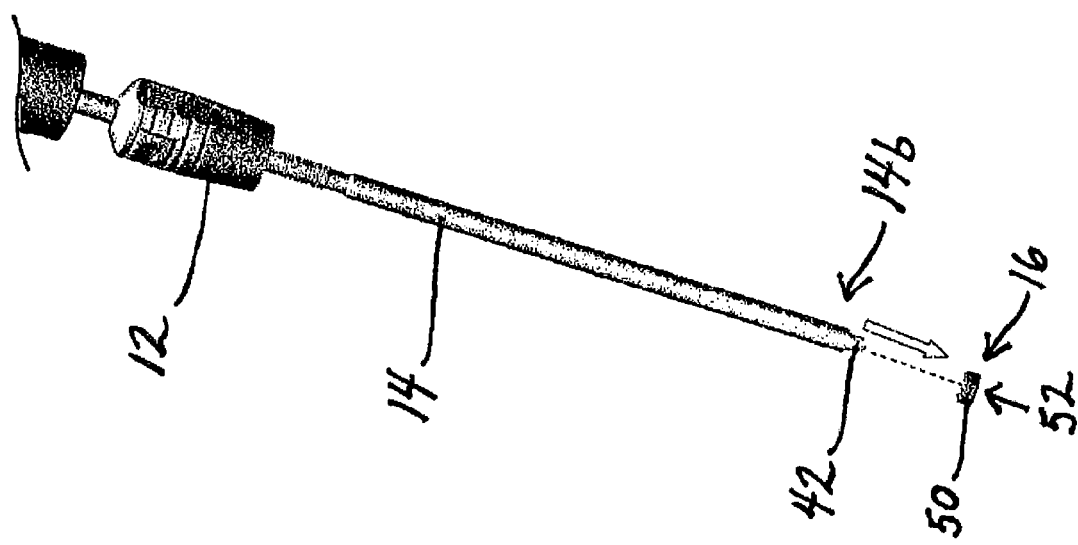
FIG. 5A is a perspective view of a rod reduction system according to one embodiment of the present invention.

As indicated above, the rod reduction system 10 can also include a fastener 16 that is retained by a fastener-retaining member 42 disposed on a distal portion 14b of the drive rod 14 as shown, for example, in FIGS. 5A-B. While a variety of fastener types are known in the art, the fastener 16 generally can be a set screw with a bore extending therethrough. The set screw can include threads formed on an outer surface thereof that are adapted to mate to threads formed in a rod-receiving opening of a spinal anchor. In one embodiment, the threads of the set screw can be timed with the threads of the drive rod to prevent over-rotation and over-tightening of the fastener. The bore extending through the set screw can have a variety of cross-sections including, for example, round, square, hexagonal, and other geometric shapes.

The fastener-retaining member 42 can take a variety of forms, the exact configuration of which will depend on the type of fastener 16 being applied. In an exemplary embodiment, shown in FIG. 5A, the fastener 16 is a set screw 50 with a hexagonal bore 52 extending therethrough. As shown, the fastener-retaining member 42 has a complementary shaped hexagonal cross section. The distal end 14b of the drive rod 14 can be passed through the bore 52 in the fastener 16 such that the fastener 16 is engaged by the hexagonally shaped fastener-retaining member 42 and retained by interference fit. FIG. 5B illustrates that the distal tip of the drive rod 14 protrudes through the fastener 16 to serve as the reduction tip 44, which will be discussed below in detail. Although the fastener 16 and fastener-retaining member 42 are shown and described as having a hexagonal cross section, one skilled in the art will appreciate that the size and shape of the fastener-retaining member 42 will vary with size and shape of the bore 52 extending through the fastener 16.

Other configurations for the fastener-retaining member 42 include spring and cam tips that can also be adapted to retain a fastener 16 by interference fit. For example, in one exemplary embodiment, shown in FIGS. 9-10, the drive rod includes an inner cam shaft 96 that is adapted to separate a split tip 98a of an outer shaft 98 to thereby engage a fastener 16 by interference fit. The fastener 16 can be released by translating the inner cam shaft 96 proximally to cause the split tip 98a of the outer shaft 98 to close.

The drive rod 14 can also include a reduction tip 44 that is disposed distal to the fastener 16 disposed on the drive rod 14 and is adapted to reduce a rod into a rod-receiving opening of a spinal anchor. A variety of configurations are available for the reduction tip 44. For example, in an exemplary embodiment, shown in FIGS. 5A-5B, the reduction tip 44 is the rigid distal end of the drive rod 14 that extends through the bore 52 in the fastener 16 and protrudes distally from the fastener 16. In use, as the drive rod 14 is advanced through the cap 12, the reduction tip 44 can contact and apply a force to a spinal rod (not shown) disposed within or adjacent to a rod-receiving opening of a spinal anchor (not shown) to thereby reduce the rod into the opening. As shown, the reduction tip 44 is conical or pointed, however, one skilled in the art will appreciate that the reduction tip 44 can include a contoured surface that is complementary to a spinal rod. In another embodiment, the reduction tip 44 can also be rounded to reduce notching of the rod during reduction.

In another exemplary embodiment (not shown), the reduction tip 44 can be movable or non-rigid. For example, in one embodiment, the reduction tip 44 can be spring loaded such that it can retract to allow a fastener 16 retained by the fastener-retaining member 42 to fully seat into a rod-receiving opening of a spinal anchor. The drive rod 14 can also include spiral cuts to allow flexing and/or axial compression of the rod when the fastener 16 contacts the rod-receiving opening of the spinal anchor to allow the fastener 16 to align itself with the threads formed in the rod-receiving opening. In yet another embodiment, the reduction tip 44 can be pivotably coupled to the drive rod 14 and adapted to remain stationary while the drive rod 14 is rotated with respect to the cap 12.

Figure 7B:
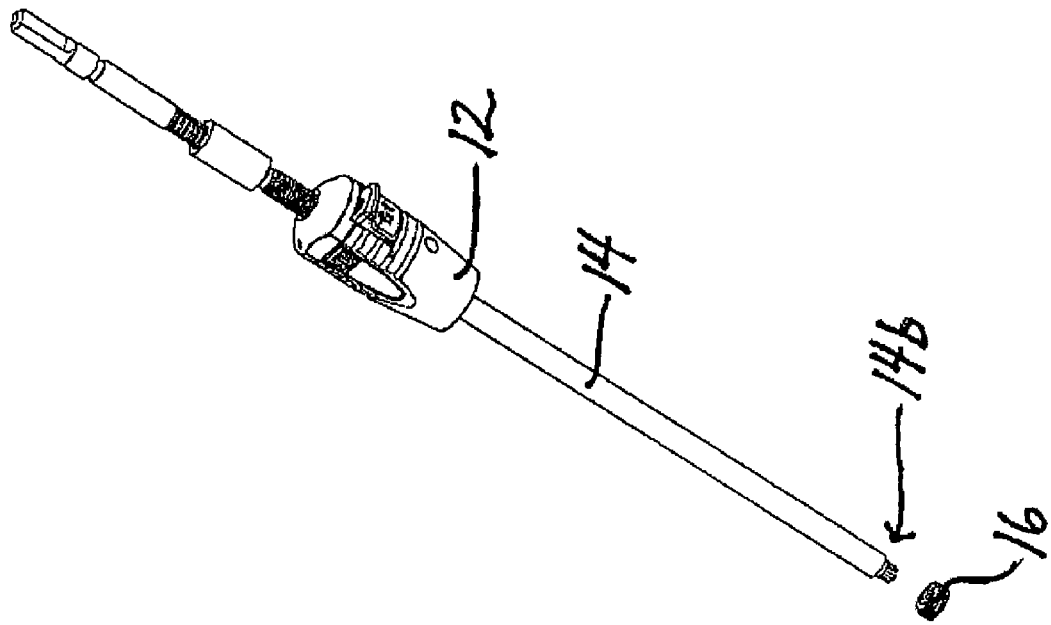
FIG. 7B is a perspective view of the system shown in FIG. 7A showing the drive rod of the system engaged with the cap of the system.
Figure 7A:
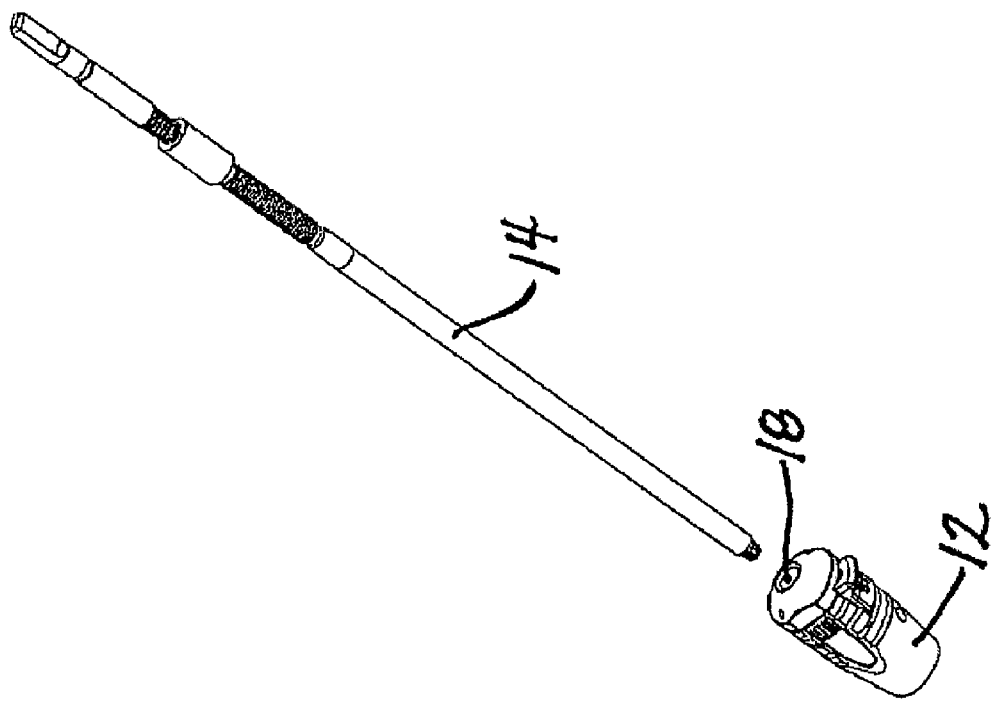
FIG. 7A is a perspective view of a rod reduction system according to one embodiment of the present invention showing the drive rod of the system disengaged from the cap of the system.

FIGS. 7A-7B illustrate the assembly of an exemplary embodiment of the rod reduction system 10 disclosed herein. As shown, the drive rod 14 is received by the bore 18 that extends through the cap 12, and the distal end 14b of the drive rod 14 slidably engages the fastener 16. FIGS. 8A-8B show the assembled rod reduction system 10 in use with a spinal implant assembly 80.

A procedure can begin by forming a minimally invasive percutaneous incision through tissue located adjacent to a desired implant site. Once the incision is made, a spinal anchor 82 and access device, such as an extension member 84, can be delivered to the anchor site. In one embodiment, the anchor 82 can be inserted through the incision with the extension member 84 attached thereto and extending through the skin incision and outside of the patient's body. In another embodiment, the extension member 84 can be attached to the anchor 82 once the anchor 82 is secured in the bone. The anchor 82 can be driven into bone using a tool, such as a driver. When the spinal anchor 82 is fully implanted, the rod-receiving opening 82a of the anchor 82 will be located adjacent to the bone such that it is either in contact with the bone or relatively close to the bone. The extension member 84 will extend from the rod-receiving opening 82a and through the skin incision, thereby providing a pathway that spans through the skin incision to the anchor 82. Additional spinal anchor 82 and access devices can be implanted in adjacent vertebrae using the same technique, or using other techniques known in the art.

Once the anchor 82 is implanted, the extension member 84 can be used to deliver various spinal connectors, fasteners, and other tools and devices to the implant site. For example, a spinal connector, such as a spinal rod 100 (shown in FIGS. 9 and 10), can be introduced through the extension member and positioned within the spinal anchor, and optionally within one or more additional spinal anchors implanted in adjacent vertebrae. Due to the alignment of the anchors, however, it can be difficult to fully seat the rod within each rod-receiving openings of the implanted spinal anchors. Thus, the rod reduction system can be used to reduce the spinal anchor into the rod-receiving openings of the spinal anchors.

As shown in FIGS. 8A-8B, the cap 12 is mated to a proximal end 84a of an extension member 84 that extends proximally from a spinal anchor 82. The drive rod 14 can be received by the bore 18 in the cap 18 to allow the drive rod 14 to extend through the cap 12 and the extension member 84. A fastener 16 can be secured to the drive rod 14 once the rod 14 is through the bore 18 in the cap 12 or the drive rod 14 can include a pre-loaded fastener 16. The rod reduction system 10 can be mated to the spinal implant assembly 80 as a whole or the cap 12 can be attached first followed by the insertion of the drive rod 14. To reduce the rod, the cap 12 can engage the drive rod 14 to advance the drive rod 14 and pre-loaded fastener 16 through the extension member 84. In an exemplary embodiment, engaging the cap can include establishing a threaded connection between a portion of the drive rod and a portion of the cap to enable longitudinal translation of the drive rod upon rotation of the drive rod. Engaging the cap can further include rotating the drive rod with respect to the cap to advance the drive rod through the cap and extension member and bring the reduction tip of the drive rod in contact with a spinal rod. Continued rotation of the drive rod can be effective to cause the reduction tip to apply a downward force to the spinal rod thereby reducing the rod into the rod-receiving opening of the spinal anchor. In an alternative embodiment, the fastener 16 can apply the downward force to the spinal rod.

The fastener is also applied to the spinal anchor to lock the spinal rod within the rod-receiving opening of the spinal anchor. Rotation of the drive rod with respect to the cap can be effective to thread the fastener within the rod-receiving opening of the anchor. As explained above, a clutch mechanism that is associated with the drive rod can be provided to disengage the driving element of the drive rod from the rod to allow the fastener to be properly aligned with the rod-receiving opening of the anchor and/or to disengage a handle portion of the drive rod from a driver portion of the drive rod to prevent over-rotation and over-tightening. FIG. 8B illustrates that as the drive rod 14 is advanced through the cap 12, a distal end 46a' of the clutch 46 abuts a proximal end 12a of the cap 12. Continued advancement of the drive rod 14 can be effective to push the clutch 46 toward a proximal end 14a of the drive rod 14 and thereby disengage the threaded portion 40a from the drive rod 14. Upon disengagement of the threaded portion 40a, the fastener 16 can be aligned with the rod-receiving opening of the anchor and secured therein. The rod reduction system can then be removed from the spinal implant assembly as a whole by de-coupling the cap from the extension member.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A rod reduction system for placing a spinal fixation rod into a rod receiving opening in a spinal anchor and installing a fastener to secure the rod to the spinal anchor, comprising:
   a cap having a bore extending therethrough, a driving element, and a mating element disposed on a distal end thereof and adapted to removably mate the cap to a spinal anchor;
   an elongate drive rod adapted to extend through the bore and having a driving element that cooperates with the driving element of the cap to form a driving mechanism; and
   a fastener disposed on a distal portion of the elongate drive rod;
   wherein actuation of the driver mechanism is effective to advance the drive rod through the cap to thereby reduce a spinal rod into a rod receiving opening of the spinal anchor and install the fastener to secure the rod to the spinal anchor;
wherein the driving element on the drive rod includes threads formed on a proximal portion thereof and adapted to engage the threads formed in the bore of the cap; and
wherein the threads on the drive rod are timed with threads formed on the fastener.

2. The system of claim 1, further comprising a screw extension attached to the spinal anchor and extending proximally from the anchor to provide access to the rod receiving opening, the cap being mated to a proximal end of the screw extension.

3. The system of claim 1, wherein the elongate drive rod includes a fastener-retaining member formed on a distal portion thereof and a reduction tip disposed distal to the fastener and adapted to reduce a rod into a rod-receiving opening of a spinal anchor.

4. The system of claim 3, wherein the fastener-retaining member comprises a spring tip having a square cross-section.

5. The system of claim 3, wherein the fastener-retaining member comprises a split tip.

6. The system of claim 3, wherein the fastener-retaining member comprises a cam tip.

7. The system of claim 3, wherein the reduction tip is spring loaded such that it can retract to allow a fastener retained by the fastener-retaining member to fully seat into a rod-receiving opening of a spinal anchor.

8. The system of claim 3, wherein the reduction tip is pivotably coupled to the drive rod and adapted to remain stationary while the drive rod is rotated with respect to the cap.

9. The system of claim 1, wherein the driving element on the cap includes threads formed in at least a portion of the bore.

10. The system of claim 9, wherein the driving element on the drive rod includes threads formed on a proximal portion thereof and adapted to engage the threads formed in the bore of the cap.

11. The system of claim 1, wherein the driver mechanism includes a threaded member having at least a partial thread formed in at least a portion of the bore, the threaded member being selectively engageable in (1) a drive rod rotation configuration in which the partial thread is engaged with threads formed on a proximal portion of the rod to permit longitudinal translation of the rod upon rotation of the rod and (2) a translation configuration in which the threaded member is disengaged from the threads on the rod to permit longitudinal translation of the rod upon translation of the rod without rotation of the rod.

12. The system of claim 11, wherein the driver mechanism further includes a locking mechanism adapted to secure the driver mechanism in the drive rod configuration.

13. A rod reduction system for placing a spinal fixation rod into a rod receiving opening in a spinal anchor and installing a fastener to secure the rod to the spinal anchor, comprising:
a cap having a bore extending therethrough, a driving element, and a mating element disposed on a distal end thereof and adapted to removably mate the cap to a spinal anchor;
an elongate drive rod adapted to extend through the bore and having a driving element that cooperates with the driving element of the cap to form a driving mechanism and having a clutch disposed on a proximal portion thereof and adapted to disengage the driving element of the rod from the rod to enable alignment of the fastener; and
a fastener disposed on a distal portion of the elongate drive rod;
wherein actuation of the driver mechanism is effective to advance the drive rod through the cap to thereby reduce a spinal rod into a rod receiving opening of the spinal anchor and install the fastener to secure the rod to the spinal anchor.

14. A rod reduction system for placing a spinal fixation rod into a rod receiving opening in a spinal anchor and installing a fastener to secure the rod to the spinal anchor, comprising:
a cap having a bore extending therethrough, a driving element, and a mating element disposed on a distal end thereof and adapted to removably mate the cap to a spinal anchor;
an elongate drive rod adapted to extend through the bore and having a driving element that cooperates with the driving element of the cap to form a driving mechanism and having a clutch disposed on a proximal portion thereof and adapted to disengage a handle portion of the rod from a driver portion of the rod to prevent over-rotation of the drive rod; and
a fastener disposed on a distal portion of the elongate drive rod;
wherein actuation of the driver mechanism is effective to advance the drive rod through the cap to thereby reduce a spinal rod into a rod receiving opening of the spinal anchor and install the fastener to secure the rod to the spinal anchor.

15. A spinal fixation system comprising:
a spinal rod,
a plurality of bone anchors, one or more of the bone anchors having a U-shaped channel for receiving a spinal rod therein and a set screw, the U-shaped channel defined by two spaced-apart arms, the set screw having an external thread engagable with an internal thread provided on the arms to secure a spinal rod in the U-shaped channel,
a plurality of generally tubular screw extensions, one or more of the screw extensions connectable to one of the bone anchors and having a central lumen extending from a proximal end to a distal end of the screw extension, the central lumen sized to receive instruments and implants therethrough,
a reduction cap having a bore extending therethrough, an internally threaded driving element, and a mating element disposed on a distal end thereof and adapted to removably mate the cap to one of the screw extensions,
a set screw driver comprising:
a proximal handle,
a drive shaft terminating at a distal end sized and shaped to fit within a mating feature on the set screw of a bone anchor, the drive shaft having an externally threaded driving element engagable with the internally threaded drive element of the reduction cap when the drive shaft is positioned within the bore of the reduction cap, and
a clutch connecting the proximal handle to the drive shaft and permitting selective rotation of the drive shaft by the proximal handle, the clutch selectively disengaging the proximal handle from the drive shaft to prevent over rotation of the drive shaft.

* * * * *